United States Patent [19]

Hechenbleikner et al.

[11] 4,267,358
[45] May 12, 1981

[54] PHENOLIC ESTER INHIBITOR

[75] Inventors: Ingenuin Hechenbleikner, Cornwall; William P. Enlow, Falls Village; James H. Weis, South Kent, all of Conn.

[73] Assignee: Borg-Warner Corporation, Chicago, Ill.

[21] Appl. No.: 129,877

[22] Filed: Mar. 13, 1980

[51] Int. Cl.³ .................................................. C07C 69/88
[52] U.S. Cl. ........................................ 560/75; 560/59; 260/45.85 B
[58] Field of Search ........................... 560/75, 238, 59

[56] References Cited

U.S. PATENT DOCUMENTS

| 1,708,902 | 4/1929 | Schalch et al. | 560/238 |
|---|---|---|---|
| 3,247,240 | 4/1966 | Meier | 560/75 |
| 3,649,667 | 3/1972 | Song et al. | 560/75 |
| 3,944,594 | 3/1976 | Kleiner | 560/75 |
| 4,085,132 | 4/1978 | Park | 560/75 |

FOREIGN PATENT DOCUMENTS

| 2512895 | 6/1976 | Fed. Rep. of Germany | 560/75 |
|---|---|---|---|
| 2706937 | 8/1978 | Fed. Rep. of Germany | 560/75 |
| 52-39646 | 3/1977 | Japan | 560/75 |
| 1324055 | 7/1973 | United Kingdom | 560/75 |

OTHER PUBLICATIONS

Chem. Abst., vol. 81, 50593p, 1974.

Primary Examiner—Paul J. Killos
Attorney, Agent, or Firm—Joseph Shekleton

[57] ABSTRACT

Phenolic esters wherein the phenolic groups are hindered by at least one ortho substituent. The esters are effective to impart thermal stability to olefin polymers. Their structure is as follows:

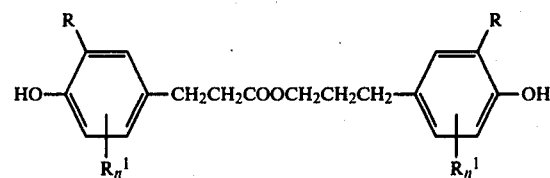

where R is alkyl or cycloalkyl of 3–8 carbon atoms, $R^1$ is alkyl of 1–6 carbon atoms and n is 1–2.

2 Claims, No Drawings

PHENOLIC ESTER INHIBITOR

BACKGROUND OF THE INVENTION

This invention relates to novel compounds which are effective to improve the heat stability of olefin polymers. It relates more particularly to olefin polymer compositions which contain such novel compounds. Still more particularly, it relates to a method for preparing such compounds.

Generally, polymer compositions are vulnerable to deterioration of physical and chemical properties during manufacture, storage, processing and use. To overcome such deterioration, or at least to inhibit it, there have been developed additive systems for the purpose of stabilizing polymeric materials with respect to physical and chemical degradation caused by exposure to environmental conditions. All of these additive systems, however, while effective for their intended purpose, are characterized by one or more shortcomings.

Olefin polymer compositions are especially vulnerable to oxidative degradation. The relatively high temperatures required for their customary processing procedures, such as roll milling, injection molding, extrusion and the like, invariably promote oxidation because these processes are carried out under ordinary atmospheric conditions, i.e., they are exposed to the oxygen of the atmosphere.

The significance of polymer oxidation lies in the adverse effect it has on polymer rheology, morphology, color, clarity, glass and other physical properties. Impact strength may be lost; the surface may become crazed or cracked. Even a darkening of the color may provide a sufficient aesthetic disadvantage as to render the polymer material unsuitable for its intended use.

SUMMARY OF THE INVENTION

The invention of this application is a phenolic ester having the structural formula:

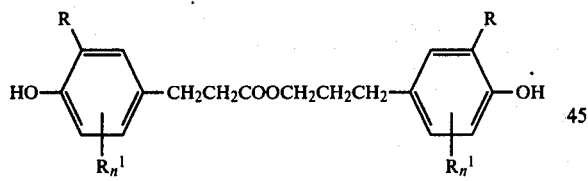

where R is an alkyl or cycloalkyl group having 3–8 carbon atoms, $R^1$ is an alkyl group having 1–6 carbon atoms, and n is 1 or 2.

Preferably, R is a bulky group, i.e., one which provides steric hindrance with respect to the phenolic group ortho to it. Tertiary alkyl groups are illustrative and tertiary butyl is especially preferred. Other illustrative specific embodiments include isopropyl, sec-butyl, tertiary amyl, 2,2-dimethylbutyl, 2,2-dimethylamyl, 2,2,3-trimethylbutyl, 2,2,3,3-tetramethylbutyl, 2,2,3,4-tetramethylamyl, cyclopentyl, cyclohexyl, 2-methylcyclohexyl and 2,4-dimethylcyclohexyl groups. Secondary and primary alkyl groups are also contemplated, such as n-butyl, n-hexyl and n-octyl.

$R^1$ is an alkyl group having 1–6 carbon atoms. Illustrative species include methyl, ethyl, n-propyl, isopropyl, n-butyl, sec-butyl, tertiary butyl and the like.

Preferably, there is but one $R^1$ and it also is a bulky group, e.g., a tertiary alkyl, and occupies the other ortho position with respect to the phenolic hydroxyl group. In another preferred case, n is 2 and the two $R^1$ groups are in the 5- and 6-positions. Two particularly preferred aromatic groups in the above structural formula are 4-hydroxy-3,5-ditertiarybutylphenyl and 4-hydroxy-3-tertiarybutyl-5,6-dimethyl phenyl.

These phenolic esters are notably effective to impart thermal stability to olefin polymers. That is, an olefin polymer composition containing a small proportion of such an ester will be resistant to deterioration ordinarily resulting from exposure to elevated temperatures.

They may be prepared by a Canizzaro reaction of a 3-(4-hydroxyphyenyl)propionaldehyde with itself, as illustrated by the following equation:

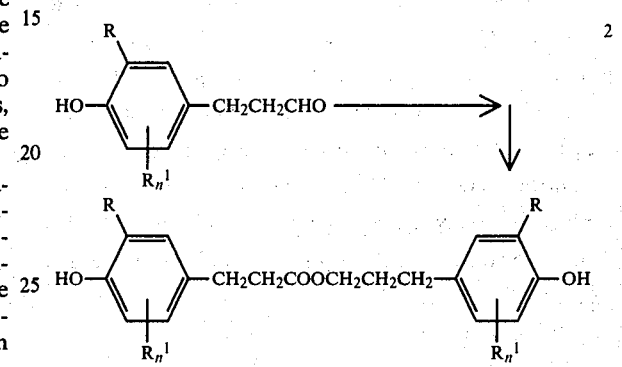

where R, $R^1$ and n are as defined earlier herein. The reaction proceeds in the presence of an inorganic alkaline catalyst such as sodium methoxide, sodium hydroxide, potassium butylate, potassium ethoxide, aluminum isopropoxide, etc. The reaction is carried out at relatively low temperatures, i.e., from about 50° C. to about 150° C., although temperatures within the range of from about 50° C. to about 225° C. are contemplated.

Alternatively, the phenolic esters of the invention may be prepared by a transesterification reaction wherein a 3-(4-hydroxyphenyl)propanol is reacted with a methyl ester of a 3-(4-hydroxyphenyl)propanoic acid. The reaction proceeds normally, with an acidic or basic catalyst.

Illustrative examples are as follows:

EXAMPLE 1

A mixture of 26.2 grams (0.1 mol) of 3-(4-hydroxy-3,5-ditertiarybutylphenyl)propionaldehyde and 1.5 g. (0.007 mol) of aluminum isopropoxide is prepared by melting each first, and adding one to the other as liquids. The mixture is heated with stirring at 100° C. for one hour. A moderately exothermic reaction ensues. Infrared analysis of the product mixture indicates conversion of the aldehyde to an ester.

The mixture is stripped on a Rotovac and the residue taken up in 50 ml. of heptane and washed with 20 ml. of saturated aqueous sodium carbonate, then with water. The residue is a viscous orange liquid weighing 19.0 grams (72% of the theory), soluble in heptane and methanol. Dissolution in pentane followed by cooling gives 15.0 grams of a solid melting at 103°–6° C.

EXAMPLE 2

A mixture of 14.0 grams (0.05 mol) of 3-(4-hydroxy-3,5-ditertiarybutylphenyl)propanol, 14.6 grams (0.05 mol) of methyl 3-(4-hydroxy-3,5-ditertiarybutylphenyl) propionate, 30 grams of a molecular seive (type 5A), 0.5 gram of sodium methylate and 200 ml. of benzene is heated at reflux temperature for two hours, then filtered. The filtrate is stripped to dryness, leaving 27.0 grams of a green, viscous liquid. This liquid residue is dissolved in 100 ml. of pentane and the resulting solution shown by infrared analysis to contain the desired ester in substantially pure form. Upon standing, 18.0 grams of a colorless crystalline precipitate forms and is collected on a filter. Recrystallization from pentane yields 17.0 grams, M.P., 103°–106° C.

The efficacy of the phenolic esters herein is shown by the data set out in the Table below. That data is obtained from a heat stability test wherein plaques of 25-mil and 100-mil thickness are rotated in an oven at 150° C. until the appearance of surface crazing, at which point they are deemed to have failed. The plaques are injection molded from material that has been extruded into pellets. Each of the test plaques consists essentially of the following:

100 parts polypropylene
0.10 part calcium stearate
0.25 part distearyl thiodipropionate plus indicated amounts of the phenolic ester. Each reported result is an average of three actual test results.

TABLE

| Phenolic ester | Amount | Rating (hours to failure) 25-ml. | 100-mil |
|---|---|---|---|
| 1. Product of Example 2 | 0.4 part | 453 | — |
| 2. Product of Example 2 | 0.2 part | 333 | 693 |
| 3. — | none | 309 | 378 |

It will be seen that the presence of a small proportion of the phenolic ester of the invention is effective to impart a high degree of heat stability to polypropylene compositions.

All parts and percentages herein, unless otherwise expressly stated, are by weight.

We claim:

1. A phenolic ester having the structure

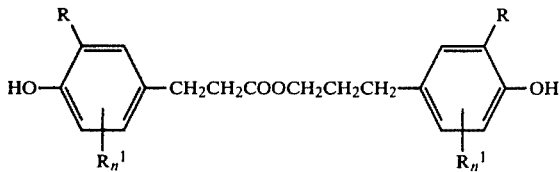

where R is an alkyl or cycloalkyl group having 3–8 carbon atoms, $R^1$ is an alkyl group having 1–6 carbon atoms, and n is 1–2.

2. The phenolic ester of claim 1 wherein R is a tertiary alkyl group.

* * * * *